United States Patent [19]

Duc et al.

[11] 4,104,123

[45] Aug. 1, 1978

[54] PROCESS OF PRODUCING A "XANTHEMONAS-TYPE" POLYSACCHARIDE

[75] Inventors: Nguyên-Công Duc, Oulchy-le-Chateau; Jean-Louis Marie Brehant, Amiens; Benoît-Joseph Pons, Languevoisin Nesle; Maurice Henri Séchet, Nesle, all of France

[73] Assignee: Les Produits Organiques du Santerre Orsan, Paris, France

[21] Appl. No.: 732,139

[22] Filed: Oct. 13, 1976

[30] Foreign Application Priority Data

Oct. 23, 1975 [FR] France .................................. 75 32498

[51] Int. Cl.$^2$ ..................... C12D 13/04; C12K 1/00
[52] U.S. Cl. ..................................... 195/31 P; 195/96
[58] Field of Search ................... 195/31 P, 96, 114; 536/1

[56] References Cited

U.S. PATENT DOCUMENTS

| 3,594,280 | 7/1971 | Colin et al. ......................... 195/31 P |
| 3,773,752 | 11/1973 | Buchanan et al. ............. 195/31 P X |

OTHER PUBLICATIONS

Vancura et al., "Nutritional requirement of Xanthomonas phaseoli", *Chemical Abstracts*, vol. 70, No. 23, pp. 91, 92, (1969), abs. no. 103881n.

Reddy et al.,"In vitro nutrition of Xanthomonas alfalfae causal orgnismkl of bacterial leaf spot of alfalfa.", *Chemical Abstracts*, vol. 77, No. 17, p. 196 (1972) abs. no. 111296k.

Kado et al., "Selective media for the isolation of Agrobacterium, Corynebacterium, Erwinia, Pseudomonas, and Xanthemonas", *Chemical Abstracts*, vol. 73, No. 15,p. 110 (1970) abs. no. 74180n.

Kotasthane et al., "Utilization of amino acids as sole source of carbon and nitrogen by some xanthemonads.", *Chemical Abstracts*, vol. 66, No. 25, pp. 10502, 10503, (1967) abs. no. 113126b.

*Primary Examiner*—Raymond N. Jones
*Assistant Examiner*—Thomas G. Wiseman
*Attorney, Agent, or Firm*—Kenyon & Kenyon, Reilly, Carr & Chapin

[57] ABSTRACT

The method of the invention, to produce a polysaccharide of the xanthane type, makes use of a strain of Xanthemonas, notably of the strain no. ATCC 31 176 deposited on Oct. 14, 1975, which is cultivated on a medium with 5 to 55 g/l or more of carbohydrates and comprising at least one amino-acid selected from glutamic acid, glutamine, arginine, tyrosine, threonine, aspartic acid, asparagine, proline, leucine tryptophane and other amino-acids giving a production of polysaccharide at least equal to 50% of that yielded by corn steep liquor, the total nitrogen of said medium being 0.1 g/l to 5 g/l; the fermentation is carried out at 25°–35° C under aerobiosis.

20 Claims, 1 Drawing Figure

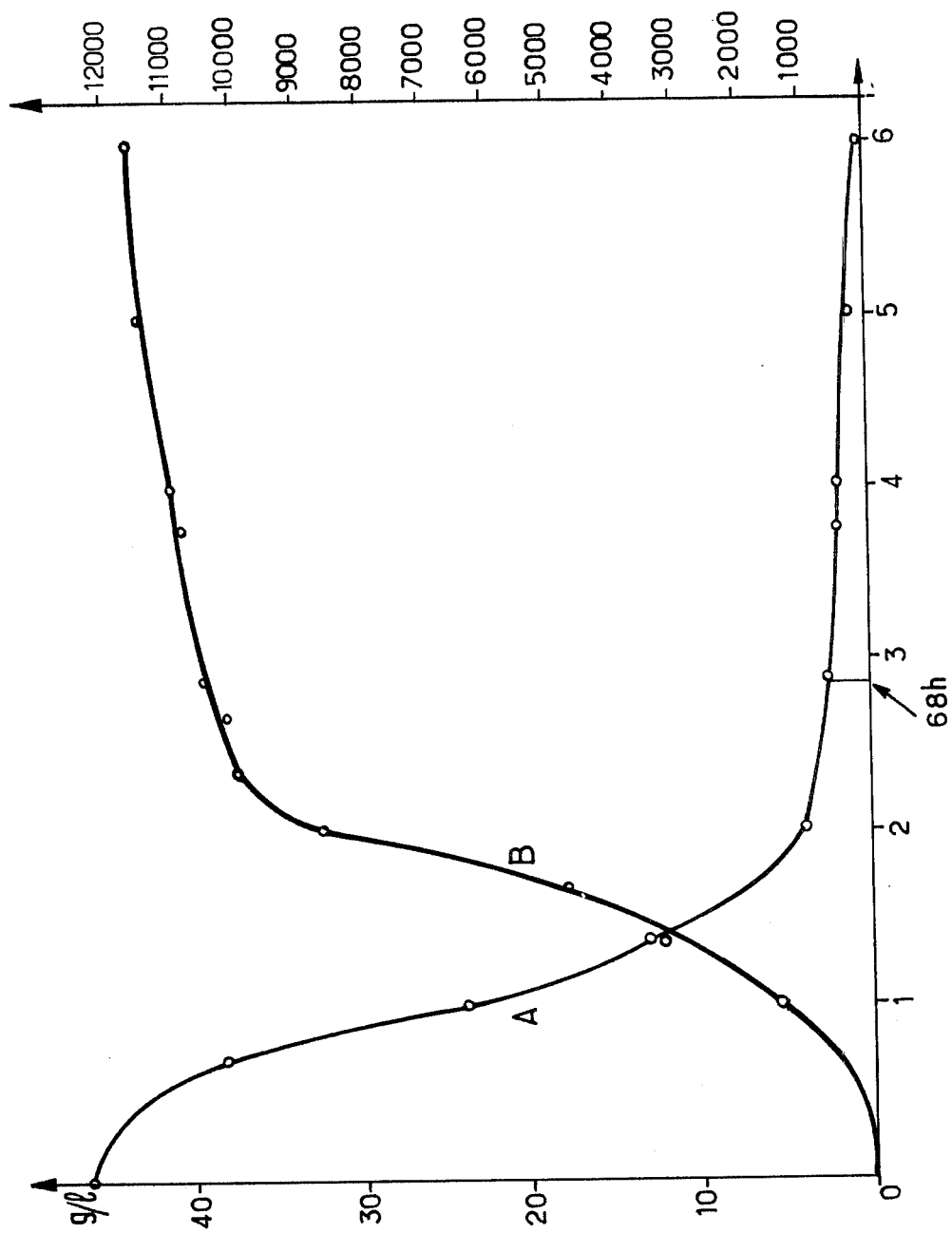

PROCESS OF PRODUCING A "XANTHEMONAS-TYPE" POLYSACCHARIDE

The present invention relates to a method of manufacturing through fermentation biopolymers consisting of xanthane type polysaccharidic gums. It is also concerned with novel strains of the Xanthomonas bacterium used in this method as well as the process of isolating or separating said strains. Finally the invention is also directed to the products or substances obtained by or resulting from said fermentation method.

For many years a great interest has been shown in thickening compositions with rheologic properties which are not very sensitive to environmental physical conditions such for instance as those compositions which are based on certain polysaccharides. Such compositions are applicable in the petroleum or oil industry, in the food industry as a thickening agent or also in many other industries covering very various fields (pharmaceuticals, textiles, explosives etc).

A particularly interesting polysaccharide is the one produced by bacteria of the Xanthomonas kind. Investigations and comparative tests have shown that this substance which is a polymer containing mannose, glucose, glucorinic acid salts and acetyl and pyruvic radicals exhibits a thickening power or capacity higher than that of dextranes and related polysaccharides as well as rheologic properties very little sensitive to pH and temperature conditions.

Since E. A. Cooper and J. F. Preston have shown in 1935 that bacteria which are parasites on plants (Enzyme formation and Polysaccharide synthesis by bacteria; Biochem. J. 29, 2267–2277) would produce polysaccharides many works for the biochemical obtainment of polysaccharides have been published. The micro-organisms used belong as a general rule to the Xanthomonas kind and more specifically to the *Xanthomonas campestris* species (the most used one), *Xanthomonas begoniae* species, *incanae* species, *vesicatoria* species, *phaseoli* species etc although Arthrobacter strains have also already been proposed. The fermentation media proposed contain at least one source of carbon and a source of nitrogen, the phosphate ion and trace elements; the pH and temperature are of about 6 to 8.5 and 25° to 35° C during fermentation.

The fermentation processes used are usually performed within aerated and stirred or shaken fermentating agents from an aqueous medium in which sugar (the most generally used source of carbon) is present at contents of about 15 to 30 grams per liter. The source of nitrogen is selected among substances containing complex nitrogen such as "dry distillation draffs or spent grains", peptones, yeast extracts, corn steep liquors etc.

Some processes also make use of substances providing both the source of carbon and the source of nitrogen, such as for instance the process using cornflours.

In all of these processes the most widely used bacterium strain is a *Xanthomonas campestris* and more particularly the *Xanthomonas campestris* NRRL-B-1459.

The present invention provides a novel method of making such polysaccharides of the xanthane type through fermentation of a suitable substrate by means of novel Xanthomonas strains said method enabling achievement of improved polysaccharides output or yield resulting in an increase in the viscosity of the medium at the end of fermentation with respect to the already known processes using *Xanthomonas campestris* and a conventional complex organic source of nitrogen.

The method of manufacture according to the invention is of the kind consisting in carrying out the fermentation of a medium with a carbon and nitrogen sources basis at pH of about 5.5 to 9 and at a temperature of about 25° to 35° C which is inoculated together with a micro-organism of the Xanthomonas kind this method being characterized in making use of a strain of Xanthomonas showing a satisfactory growth on a medium only containing one of the amino-acids of the following first series: glutamic acid, glutamine, arginine, tyrosine, threonine, aspartic acid, asparagine, proline, leucine and tryptophane and in using as a fermentation medium a medium with a content of 5 g/l to 55 g/l or more of carbohydrates and containing at least one amino-acid selected from the group consisting of those of said first series as well as any other amino-acids giving a yield or production of polysaccharide at least equal under the same conditions and with the same content in total nitrogen to 50% of that yielded by the corn steep liquor, the source of nitrogen corresponding to 0.1 g/l to 5 g/l and preferably 0.2 g/l to 2 g/l of total nitrogen.

With the terms "satisfactory growth" is meant that the micro-organism is likely to develop and to give a production output of polysaccharides which in terms of viscosity is higher by at least 20% to that achieved under the same conditions and with the same total nitrogen content by using the strain of *Xanthomonas campestris* NRRL-B-1459 in the presence of the amino-acids of said first series.

Such an increase in yield or output may in particular be appreciated through the following test considered as a possible reference test for the definition of the terms "satisfactory growth":

As a production medium is used the one of test B of example 1 stated hereinafter, viz.:

| Glucose | 30 | g |
| $K_2HPO_4$, $3H_2O$ | 5 | g |
| $MgSO_4$, $7H_2O$ | 0.1 | g |
| Source of nitrogen | 0.72 | g of total nitrogen |
| Mains or tap water | 1 | l. |

The process is performed under the conditions of that test (pH:7.5; 30° C; 4 days; 200 r.p.m.) while effecting inoculation:

with *Xanthomonas campestris* NRRL-B-1459 on the one hand, with the Xanthomonas strain according to the invention on the other hand with the source of nitrogen being exactly the same in both instances and consisting only of one or several of the amino-acids of said first series.

It has also been noted that the strains according to the invention with a "satisfactory growth" in presence of the amino-acids of said first list would generally exhibit the subsidiary characterizing feature of giving very low production outputs when they were in the presence of only one or several of the amino-acids of the following second series: glycocoll, lysine, cysteine, histidine, isoleucine and serine, which will be illustrated later through a few examples.

According to a preferred embodiment of the present invention 70 to 100% of total nitrogen of the source of nitrogen of the fermentation medium are represented by the nitrogen of the amino-acids of said first series.

A characterizing feature which is common to the amino-acids of the first series consists also in that when they are used as the only source of nitrogen in the production medium they would result in polysaccharide outputs higher than those obtained when using corn steep liquor as the only source of nitrogen under the same conditions and with the same total nitrogen content; the polysaccharide output or yield may be estimated by means of a viscosity measurement with a Brookfield viscosimeter; in other words the amino-acids of said first series would give higher viscosities than those obtained with corn steep liquor whereas the amino-acids of the second series would give viscosities substantially lower than those obtained with said corn steep liquor.

The applicants have accordingly made apparent the large differences from one amino-acid to another in the interactions between the amino-acid involved and the various newly isolated strains as will be shown hereinafter so that the applicants has succeeded in developing a process leading to a substantial improvement in the polysaccharide output with respect to the conventional case of fermentation of a conventional organic source of nitrogen by means of a strain of *Xanthomonas campestris*.

The applicants have discovered that the strains it had isolated on a given amino-acid were able to develop on a large number of other amino-acids taken separately. All the amino-acids however are not equivalent. In particular the latency period is more or less extended depending upon the amino-acid involved and the final growth achieved as well accordingly as the final viscosity are more or less substantial. The applicants have discovered the outstanding property that with an equal amount of total nitrogen and for a number of amino-acids the viscosity achieved at the end of the fermentation is higher than that obtained under the same conditions for a conventional complex source of nitrogen such as a corn steep liquor and such a viscosity may in some cases be up to twice the viscosity obtained with corn steep liquor (viscosity expressed in centipoises measured with a Brookfield viscosimeter, rod LV4-30 r.p.m., unless otherwise stated).

It should also be emphasized that the amino-acid providing the highest viscosity does not always coincide with the amino-acid on which has been carried out the isolation of the strain used in the production process according to the invention. The fact of non-equivalence of all the amino-acids would account for the poor results obtained with conventional complex sources of nitrogen: these consist among others of a mixture of amino-acids in given proportions. Among those some are conducive to a high production of biopolymers and others are much less promoting but all may be used by the bacterium and this would account for the fact that at the end of the fermentation is found an amount of biopolymeres lower than the amount obtained with the most effective amino-acids such as those which have been shown up by the applicant.

According to a characterizing feature of the present invention the fermentation medium has a content of from 0.10 g/l to 20 g/l and preferably from 0.5 g/l to 5 g/l of phosphate ions in terms of dibasic potassium phosphate as well as one or several trace elements among which the magnesium ion; the magnesium ion content of the fermentation medium preferably ranges from 0.0025 g/l to 1 g/l in terms of magnesium; advantageous sources of magnesium include soluble magnesium salts such as magnesium sulfate, acetate, chloride or nitrate. The phosphate ions are in particular present within the fermentation medium as phosphoric acid or soluble phosphate for instance potassium or sodium phosphate.

The source of carbon of the fermentation medium consists at least in part of a carbohydrate which is selected preferably among glucose, starches or amylums, amylum or starch hydrolyzates, saccharose, levulose, fructose, maltose and molasses of sugar-beet or sugarcane.

According to the present invention the fermentation by means of the strains defined hereinabove is effected for a duration of 1 to 6 days under adequate aeration and stirring or shaking conditions at a pH ranging from 5.5 to 9 and preferably from 6.5 to 8 and at a temperature ranging from about 25° to 35° C and preferably from 27° to 31° C.

According to an embodiment of the present invention the source of nitrogen of the fermentation medium consists of nitrogeneous compounds of the mother-liquor of crystallization of amino-acids of said first series, for instance of the mother-liquor of crystallization of the glutamic acid which is a by-product of the manufacture of glutamic acid provided through a fermentation process or a chemical process; it should be borne in mind that the glutamic acid content of such a mother-liquor represents 60 to 80% of the total amount of the amino-acids, such a content being given in terms of nitrogen. It is also possible to use as a source of nitrogen of the fermentation medium by-products of agricultural and foodstuff origin the soluble nitrogen content of which is mainly provided by the amino-acids of said first series.

Preferably the Xanthomonas strain used in the production process according to the present invention is the one which has been filed with the "American type culture collection" 12301 Park Lawn Drive, Rockville, Md. 20852 U.S.A. under Ser. No. ATCC 31 176 on Oct. 14, 1975.

The strains used in the method of production according to the present invention and in particular the strain ATCC 31 176 referred to hereinabove may be obtained through isolation from a sick plant by using an isolating medium containing a source of carbon preferably consisting essentially of carbohydrates, trace elements and a source of nitrogen constituted at least in major part by at least one of the amino-acids from the group mentioned hereinabove and in particular one of those belonging to the first series previously defined, i.e. glutamic acid, arginine, tyrosine, threonine, aspartic acid, proline, leucine and tryptophane.

The method of isolating productive strains is preferably performed through selection from a sample of sick plant by carrying out successive cultures within an isolating medium containing as a source of nitrogen a major proportion of at least one amino-acid of said first series and preferably consisting of at least one such amino-acid.

The operating method steps are carried out for instance in the following manner according to microbiological processing techniques well known per se:

inserting a part of a plant attacked by the disease into a first fraction of an isolating medium with a gelose basis containing in particular the amino-acid selected for growth;

incubating this fraction between 27° and 31° C for 45 to 50 hours;

inoculating a small amount of that fraction on a second fraction of the same medium (by operating for instance as follows: retaking the most isolated yellow and viscous colonies with a platinum snare or loop and effecting a streak culture from each isolated colony onto said second fraction);

incubating again between 27° and 31° C for 45 to 50 hours;

taking the isolated yellow colonies having a viscous appearance and inoculating same one by one onto a third fraction of the same isolating medium within a sloping test tube and then dissociating these colonies; thereby recovering several distinct strains all of which are in accordance with the invention.

It is for instance possible to use as a plant stem fragments (sections or lengths with a thickness of 1 mm to 3 mm) of harlock (Sinapis arvensis) the disease of which is reflected by a wilting and a yellowing of the leaves; by using as an isolating medium the following medium (pH adjusted to a value of 7 by adding potassium hydroxyde):

| | | |
|---|---|---|
| Glucose | 0.2 | g |
| $K_2HPO_4$ | 0.1 | g |
| Amino-acid of the first series | 1 | g |
| $MgSO_4, 7H_2O$ | 0.01 | g |
| Mains or tap water quantum satis for | 100 | ml (pH : 7.0) |
| Gelose | 2 | g | and by operating as stated hereinabove a plurality of strains are obtained. In the case where the amino-acid is glutamic acid the strains obtained are referred to as ORS-B-243 to ORS-B-256; all of them have a yellow colour and exhibit the same microscopic and macroscopic appearance; among these strains the strain ORS-B-253 has proved to be the best producer of saccharidic biopolymers in the method of production according to the present invention.

It is that strain which has made the subject of said ATCC filing ATCC 31176).

The isolation of that particular strain has been carried out as follows.

The incubation of the third medium is effected for 48 hours at 30° C, and then the test tube is set to an upright position and an equal volume of an 8% solution of NaCl is introduced therein. Then are carried out successive dilutions from 10 to 10 which are incubated for 48 hours at 30° C; the various isolated colonies are recovered and subcultured with a view of preserving same onto the same isolating medium in a sloping test tube.

The characterizing features of that strain ORS-B-253 are given in the following table in comparison with the strain of Xanthomonas campestris NRRL-B-1459; these characterizing features have been determined in the same conditions according to the conventional technological processes of microbiology from an isolated colony of each one of both strains to be compared.

Compared characteristics of *Xanthomonas campestris* NRRL-B-1459 and *Xanthomonas* species ORS-B-253

| | *Xanthomonas campestris* NRRL-B-1459 | *Xanthomonas* Sp. ORS-B-253 |
|---|---|---|
| Appearance on gelose | Round viscous yellow colonies | Round viscous yellow colonies |
| Gram | — | — |
| Gelatine | Quickly liquefied | Slowly liquefied |
| Reduction of the nitrates | — | — |
| Indole | — | — |
| Oxidase (Gordon and Mac Leod) | — | + |
| Citrate (Simmons) | — | + |
| Hugh Leifson | Oxidizing | Oxidizing |
| β-galactosidase | — | + |

-continued

Compared characteristics of *Xanthomonas campestris* NRRL-B-1459 and *Xanthomonas* species ORS-B-253

| | *Xanthomonas campestris* NRRL-B-1459 | *Xanthomonas* Sp. ORS-B-253 |
|---|---|---|
| Urease | — | — |
| Tryptophane desaminase | — | — |
| Product of acetoin | — | + |
| Arginine dihydrolase | — | — |
| Lysine decarboxylase | — | — |
| Ornithine decarboxylase | — | — |
| Tolerance to sodium chloride | 2% to 5% | 1% to 2% |

Hereafter is given a table listing the compared productions of polysaccharidic biopolymers (production output or yield given in terms of viscosity measurement) as a function of the amino-acid used as the single source of nitrogen within the production medium in the case of the strain *Xanthomonas campestris* NRRL-B-1459 and in the case of the strain ORS-B-253.

The production medium is the following:

| | | |
|---|---|---|
| glucose | 30 | g |
| $K_2HPO_4, 3H_2O$ | 5 | g |
| $MgSO_4, 7H_2O$ | 0.1 | g |
| total nitrogen | 0.72 | g |
| Mains or tap water quantum satis for | 1 | l |

| | NRRL-B-1459 | ORS-B-253 |
|---|---|---|
| Glutamic acid | 4,500 cPo | 8,800 cPo |
| Aspartic acid | 3,900 | 8,600 |
| Arginine | 4,100 | 8,700 |
| Tyrosine | 4,600 | 7,700 |
| Threonine | 6,100 | 7,480 |
| Tryptophane | 3,900 | 10,500 |
| Proline | 6,700 | 9,000 |
| Leucine | 2,400 | 8,500 |
| Phenylalanine | 2,750 | 4,600 |
| Valine | 3,750 | 3,900 |
| Alpha-alanine | 3,700 | 1,850 |
| Methionine | 3,550 | 1,750 |
| Glycocoll | <500 | <500 |
| Lysine | <500 | <500 |
| Cysteine | <500 | <500 |
| Histidine | <500 | <500 |
| Isoleucine | <500 | <500 |
| Serine | <500 | <500 |
| Mother-liquor of crystallization of glutamic acid | 3,600 | 8,200 |
| Corn steep liquor | — | 17,000 |

Now will be described various exemplary embodiments of using the method of production according to the invention, which examplary embodiments are given by way of non limiting examples; it should be noted that some of the tests relating to these examples are not part of the present invention since they make use of a corn steep liquor as the only source of nitrogen of the fermentation medium.

The single FIGURE of the annexed drawings relates to example 5.

EXAMPLE 1

Test A

From an inclined culture of the strain of Xanthomonas species ORS-B-253, 75 ml of a preculture consisting of the following medium MY are cultured or seeded:

| | | |
|---|---|---|
| Glucose | 1 | g |
| Peptone | 0.5 | g |
| Yeast extract | 0.3 | g |

-continued

| | | |
|---|---|---|
| Malt extract | 0.3 | g |
| distilled water quantum satis for | 100 | ml |
| Gelose | 2 | g |

That medium with a pH=7 is previously sterilized for 20 mn at 115° C. After culturing this preculture is caused to be incubated at 30° C on a rotary stirring device or shaker revolving at 200 r.p.m. for 24 hours.

Seven production media are prepared which differ from each other only by the source of nitrogen and the composition of which is the following:

| | | |
|---|---|---|
| Glucose | 5 | g |
| $K_2HPO_4$, $3H_2O$ | 5 | g |
| $MgSO_4$, $7H_2O$ | 0.1 | g |
| Source of nitrogen | 0.36 | g in terms of total nitrogen |
| Mains or tap water quantum satis for | 1 | l |

The pH of these production media is adjusted to 7.5 by adding phosphoric acid or potassium hydroxide depending upon the nature of the source of nitrogen prior to sterilizing the medium for 30 mn at 110° C.

The production phase is initiated by culturing 100 ml of production medium placed within a 500 ml vial by means of 5 ml of said preculture (24h old preculture).

After 2 days of incubation at 30° C on a rotary stirring device or shaker (revolving at 200 r.p.m.) the productions are stopped. The growth obtained is measured with a spectrophotometer at 650 mµ on a 1/50th dilution of the medium. The amount of biopolymers is estimated through viscosity measurement with a Brookfield viscosimeter at 30 r.p.m. with the measuring rod LV3.

The results obtained are summarized in the following table:

| Source of nitrogen selected for the production medium | Relative growth | Brookfield viscosities (LV3-30 r.p.m.) |
|---|---|---|
| Corn steep liquor | 100% | 50 ± 10 cPo |
| Glutamic acid | 74% | 110 ± 10 cPo |
| Aspartic acid | 52% | 110 ± 10 cPo |
| Arginine | 63% | 100 ± 10 cPo |
| Leucine | 72% | 110 ± 10 cPo |
| Mother liquor of crystallization of glutamic acid | 100% | 120 ± 10 cPo |

Test B

These tests are identical with the tests A except for the glucose content which is then of 30 g/l and the nitrogen source content which is then equal to 0.72 g/l in terms of total nitrogen.

After 4 days of incubation under the same conditions as in the example A the following results are obtained:

| Source of nitrogen | Brookfield viscosity (LV4-30 r.p.m.) | Source of nitrogen | Brookfield viscosity (LV4-30 r.p.m.) |
|---|---|---|---|
| Corn steep liquor | 7,000 cPo | Valine | 3,900 cPo |
| Glutamic acid | 8,800 cPo | α-Alanine | 1,850 cPo |
| Arginine | 8,700 cPo | Methionine | 1,750 cPo |
| Tyrosine | 7,700 cPo | Glycocoll | <500 |
| Threonine | 7,480 cPo | Lysine | <500 |
| Aspartic acid | 8,600 cPo | Cysteine | <500 |
| Proline | 9,000 cPo | Histidine | <500 |
| Leucine | 8,500 cPo | Isoleucine | <500 |
| Tryptophane | 10,500 cPo | Serine | <500 |
| Phenylalanine | 4,600 cPo | | |

EXAMPLE 2

The production media have the following basic composition:

| | | |
|---|---|---|
| Glucose | 30 | g |
| $K_2HPO_4$, $3H_2O$ | 5 | g |
| $MgSO_4$, $7H_2O$ | 0.1 | g |
| Total nitrogen | 0.18 | g |
| Mains or cap water quantum satis for | 1 | l |

The pH is adjusted to a value of 7.5 and the medium is sterilized for 15 mn at 121° C after distribution within 500 ml vials at a rate of 100 ml of medium per vial. According to the test the source of nitrogen is distributed in the following manner: (values in g/l in terms of total nitrogen)

| Tests | A | B | C | D | E |
|---|---|---|---|---|---|
| Corn steep liquor | 0.18 | 0.108 | 0.072 | 0.036 | 0 |
| Glutamic acid | 0 | 0.072 | 0.108 | 0.144 | 0.18 |

A preculture of the strain of Xanthomonas species ORS-B-253 prepared as in example 1 has been used for culturing at a rate of 5% the contents of the various vials which are then caused to incubate for 4 days on a stirring device of shaker at 30° C. After the 4 days the following results are obtained:

| Tests | Brookfield viscosities (LV4-30 r.p.m.) |
|---|---|
| A | 8,700 |
| B | 12,200 |
| C | 12,400 |
| D | 11,600 |
| E | 13,340 |

EXAMPLE 3

The production media have the following basic composition:

| | | |
|---|---|---|
| Glucose | 30 | g |
| $K_2HPO_4$, $3H_2O$ | 5 | g |
| $MgSO_4$, $7H_2O$ | 0.1 | g |
| Nitrogen | | according to test |
| Mains or tap water quantum satis for | 1 | l |

In test A the source of nitrogen is represented by the corn steep liquor, in test B by glutamic acid, in test C by the mother liquor of crystallization of glutamic acid. The tests are run with the strain of Xanthomonas specias ORS-B-253 as in the foregoing examples. After 4 days of incubation the results are the following:

| | Viscosities measured with a Brookfield viscosimeter (LV4-30 r.p.m.) | | |
|---|---|---|---|
| Source of nitrogen Contents in terms of total nitrogen | A Corn steep liquor | B Glutamic acid | C mother liquor of crystallization of glutamic acid |
| 0.108 g/l | 7,230 | 10,200 | 15,100 |
| 0.18 | 7,830 | 11,300 | 16,000 |
| 0.27 | 9,000 | | 16,340 |
| 0.36 | 10,300 | 16,800 | 15,600 |
| 0.72 | 12,800 | 18,700 | 18,640 |
| 1.08 | 12,700 | 12,250 | 18,480 |

EXAMPLE 4

From a 48h old inclined culture of the strain Xanthomonas species ORS-B-253 there is derived a 24h old preculture within 75 ml of the medium MY defined in example 1. This first preculture is used for culturing a second preculture in 1,500 ml of the same medium MY placed within a 6-liter vial. That second preculture is incubated on a rotary stirring device or shaker for 24 hours at 30° C.

For the culture in a 14-liter New Brunswick fermenting vat the following production medium is prepared:

| | | |
|---|---|---|
| Glucose | 385 | g (i.e. 55 g/l) |
| Glutamic acid | 70 | g (i.e. 0.95 g/l of total nitrogen) |
| $MgSO_4, 7H_2O$ | 0.7 | g (i.e. 0.1 g/l) |
| $K_2HPO_4, 3H_2O$ | 7 | g (i.e. 1 g/l) |
| Mains or tap water quantum satis for | 7 | l. |

The production medium is adjusted to a pH of 7.2 with potash and sterilized in an autoclave for 45 mn at 115° C. The fermentation is initiated by culturing the production medium with 350 ml of the second (24h old) preculture. During fermentation the pH is kept at a value of 7.2 with potash by means of an automatic control system; the temperature is maintained at 28° C. The stirring rate at the beginning of the fermentation is adjusted to 600 r.p.m. and is gradually increased up to 750 r.p.m. at the end of fermentation. The aerating rate is maintained constant and equal to 1 vol./vol.mn.

After 24 hours of fermentation the viscosity measured with a Brookfield viscosimeter (LV4-30 r.p.m.) is equal to 600 cPo. After 40 hours of fermentation it is equal to 6,300 cPo. After 55 hours it is equal to 12,000 cPo. The fermentation is discontinued after 67 hours.

The amount of residual sugar in terms of total reducing sugars is equal to 0.15 g/l and the viscosity is up to 12,600 cPo. One liter of the final broth is precipitated with alcohol and after drying of the floculate 30 g of dry polysaccharidic biopolymer are isolated.

Through hydrolysis of the polysaccharidic biopolymer and analysis of the components it is possible to find the following substances: glucose, mannose, glucuronic acid, pyruvic acid and acetic acid.

EXAMPLE 5

This test is identical with that of example 4 except for glutamic acid being substituted for by an equivalent amount, expressed in terms of total nitrogen, of mother liquor of crystallization of glutamic acid. All the other test conditions are kept identical.

After 68 hours of fermentation the viscosity is equal to 10,500 cPo. From the broth then obtained 27 g/l of polysaccharidic biopolymer in a dry condition could be isolated.

If the fermentation is continued beyond 68 hours (instead of extracting the biopolymer after the lapse of such a duration) the results obtained enable to plot curves A and B in the figure of the annexed drawing which show the residual sugar content (expressed in g/l of glucose) and viscosity (in centipoises), respectively, against the duration of fermentation (expressed in days).

EXAMPLE 6

The process is operated as in example 5 but use is made of 22 g/l of glucose (instead of 55 g/l) and 2.06 g/l of dibasic sodium phosphate (instead of 1 g/l of $K_2HPO_4, 3H_2O$): the pH is kept at 7.3 by adding sodium hydroxide.

The following results are obtained:

| Duration of fermentation | Brookfield viscosity |
|---|---|
| | (LV4-30 r.p.m.) |
| 10 h | 100 cPo |
| 24 h | 2,600 cPo |
| 32 h | 4,600 cPo |
| 40 h | 4,800 cPo |
| 48 h | 4,900 (residual sugar : 0.6 g/l) |

After 48 h of fermentation 12.5 g/l of dry polysaccharidic biopolymere are extracted.

EXAMPLE 7

The process is performed as in the foregoing example except for the use of 6 g/l of dibasic sodium phosphate and the pH value is allowed to vary without any control during the fermentation.

The following results are obtained:

| Duration of fermentation | Brookfield viscosity | residual sugars | |
|---|---|---|---|
| | (LV4-30 r.p.m.) | | |
| 16 h | 100 cPo | 11.8 | g/l |
| 24 h | 1,900 cPo | 7.0 | g/l |
| 32 h | 3,800 cPo | 1.0 | g/l |

After 32h old of fermentation 10 g/l of dry saccharadic biopolymere have been isolated.

EXAMPLE 8

The tests of this example correspond to the use of various sources of carbon.

The production media have the following composition:

| | | |
|---|---|---|
| Glutamic acid | 7.5 | g |
| $K_2HPO_4, 3H_2O$ | 5 | g |
| $MgSO_4, 7H_2O$ | 0.1 | g |
| Sugar | 30 | g (expressed in terms of glucose) |
| Mains or tap water quantum satis for | 1 | l |

The sugars used as a source of carbon are the following:

| Test A | Test B | Test C | Test D | Test E |
|---|---|---|---|---|
| Glucose | Saccharose | Molasses of sugar | Industrial corn starch | starch hydrolysate with |

-continued

| Test A | Test B | Test C | Test D | Test E |
|---|---|---|---|---|
| | | beet | or amylum | 70% of glucose |

The media (100 ml in a 500 ml vial are sterilized for 30 mn at 110° C after the pH have been adjusted to 7.5 with potash.

The culturing is effected for each vial by adding 5 ml of a preculture of the 24h old strain of ORS-B-253 prepared as in example 1.

After 4 days of incubation on a rotary stirring device or shaker at 28° C the viscosities obtained are the following (Brookfield viscosimeter LV4-30 r.p.m.):

| Test A | Test B | Test C | Test D | Test E |
|---|---|---|---|---|
| 16,000 cPo | 15,600 cPo | 14,900 cPo | 16,900 cPo | 15,200 cPo |

EXAMPLE 9

The tests of that example show various total nitrogen contents (ranging from 0.205 to 2.05 g/l).

The production medium has the following composition:

| Saccharose | 30 g |
|---|---|
| $K_2HPO_4$, $3H_2O$ | 5 g |
| $MgSO_4$, $7H_2O$ | 0.1 g |
| Mother liquor of crystallization : of glutamic acid | according to test |
| Mains or tap water quantum satis for | 1 l |

The medium is distributed in 500 ml-vials at the rate of 100 ml per vial. The total nitrogen contents are the following:

| TEST | A | B | C | D | E | F | G |
|---|---|---|---|---|---|---|---|
| Mother liquor of crystallization of glutamic acid expressed in g/l of total nitrogen | 0.205 | 0.41 | 0.615 | 0.82 | 1.23 | 1.64 | 2.05 |

The pH are adjusted to a value of 7.5 and the various media are sterilized for 30 mn at 110° C. After each medium has been cultured with 4 ml of a 24h old preculture of the strain of ORS-B-253 prepared as in example 1, the vials are caused to be incubated at 28° C on a rotary stirring device or shaker revolving at 200 r.p.m.

The results are the following: (Brookfield viscosimeter LV4-30 r.p.m.):

| Test | After 24 h of fermentation | after 48 h of fermentation |
|---|---|---|
| A | 1,000 cPo | 3,500 cPo |
| B | 1,300 cPo | 6,700 cPo |
| C | 1,350 cPo | 5,800 cPo |
| D | 1,150 cPo | 7,100 cPo |
| E | 1,150 cPo | 9,200 cPo |
| F | 650 cPo | 9,900 cPo |
| G | 600 cPo | 9,900 cPo |

EXAMPLE 10

The tests of this example relate to various pH values (ranging from 6.60 to 8.70).

The production medium has the following composition:

| Saccharose | 25 g |
|---|---|
| $K_2HPO_4$, $3H_2O$ | 5 g |
| $MgSO_4$, $7H_2O$ | 0.1 g |
| Mother liquor of crystallization of glutamic acid | 0.82 g of total nitrogen |
| Mains or tap water quantum satis for | 1 l |

This medium is distributed at the rate of 100 ml within 500 ml-vials. In each one of the vials the pH value is adjusted differently with potash or phosphoric acid and after sterilization for 30 mn at 110° C the pH values are the following:

| Test | A | B | C | D | E | F |
|---|---|---|---|---|---|---|
| pH | 6.60 | 7.15 | 7.70 | 8.15 | 8.40 | 8.70 |

The media are inoculated with 4 ml of a preculture of Xanthomonas species ORS-B-253 which is 24 h old and prepared as in example 1. After 4 days of incubation at 28° C on a rotary shaker the pH values and viscosities are the following:

| TEST | A | B | C | D | E | F |
|---|---|---|---|---|---|---|
| final pH | 5.55 | 6.20 | 6.40 | 6.60 | 6.80 | 6.90 |
| viscosity (cPo) | 6,400 | 10,000 | 10,000 | 7,000 | 7,000 | 8,300 |

EXAMPLE 11

The tests of this example correspond to the use of various phosphate ions contents.

For 1 liter of medium prepared in raw water:

| Saccharose | 30 g |
|---|---|
| $MgSO_4$, $7H_2O$ | 0.1 g/l |
| $K_2HPO_4$, $3H_2O$ | according to test |
| Mother liquor of crystallization of glutamic acid | 0.82 g of total nitrogen |
| Mains or tap water quantum satis for | 1 l |

The medium is distributed in 500 ml-vials at the rate of 100 ml per vial, as follows:

| Test | A | B | C | D |
|---|---|---|---|---|
| $K_2HPO_4$, $3H_2O$ in g/l | 12 | 10 | 5 | 0.5 |
| $PO_4^{3-}$ in g/l | 5.4 | 4.5 | 2.25 | 0.225 |

The pH values are adjusted to 7.5 and the media sterilized for 30 mn at 100° C. A 24 h old preculture of the strain ORS-B-253 is used for culturing the media at the rate of 4 ml per vial. After 2 days of incubation at 28° C on a rotary shaker revolving at 200 r.p.m. the viscosities obtained are the following:

| Test | A | B | C | D |
|---|---|---|---|---|
| Average viscosity | 8,000 cPo | 8,600 cPo | 7,800 cPo | 5,400 cPo |

It should be understood that the present invention is not at all limited to the embodiments described which have been given by way of example only. In particular it comprises all the means constituting technical equivalents of the means described as well as their combinations if same are carried out according to its gist and used within the scope of the appended claims.

What is claimed is:

1. A method of producing a Xanthane type of polysaccharide through fermentation under aerobiosis and under stirred conditions with a pH value ranging from about 5.5 to 9 and at a temperature of 25° to 35° C of an aqueous fermentation medium containing sources of carbon and of nitrogen by inoculating said aqueous fermentation medium with a strain of Xanthomonas having an increased polysaccharide production output of at least 20 percent in terms of viscosity when compared to that achieved by *Xanthomonas campestris* NRRL-B-1459 grown under the same conditions on a growth medium containing as nitrogen source any one of the amino-acids selected from the group consisting of glutamic acid, glutamine, arginine, tyrosine, threonine, aspartic acid, asparagine, proline, leucine and tryptophane, by using as said aqueous fermentation medium an aqueous medium with a content of at least 5 g/l to 55 g/l of carbohydrates and containing at least one amino-acid selected from said group as well as any other amino-acids yielding a polysaccharide producing capacity at least equal under the same conditions and with the same total nitrogen content to 50% of that yielded by corn steep liquor, the source of nitrogen of said fermentation medium corresponding to a nitrogen value ranging from 0.1 g/l to 5 g/l, and by recovering said polysaccharide from the fermented aqueous medium.

2. A method according to claim 1, wherein the source of nitrogen of said fermentation medium corresponds to a value ranging from 0.2 g/l to 2 g/l of total nitrogen.

3. A method according to claim 1, wherein 70 to 100% of the total nitrogen of the source of nitrogen of said fermentation medium is represented by the nitrogen from the amino acids of said group.

4. A method according to claim 1, wherein said fermentation medium has a content of 0.10 g/l to 20 g/l of phosphate ions expressed in terms of dibasic potassium phosphate as well as at least one trace element among magnesium ions.

5. A method according to claim 4, wherein said phosphate ion content is from 0.5 g/l to 5 g/l.

6. A method according to claim 1, wherein said strain is obtained from a sick plant by using an isolating medium containing trace elements, a source of carbon and a source of nitrogen containing a major proportion of at least one amino-acid from said group.

7. A method according to claim 6, wherein at least the major part of said source of nitrogen of said isolating medium consists of glutamic acid.

8. A method of producing a Xanthane type of polysaccharide comprising the steps of inoculating an aqueous fermentation medium containing sources of carbon and of nitrogen with a strain of Xanthomonas filed with the American Type Culture Collection under Serial No. ATCC 31 176 on Oct. 14, 1975, said aqueous medium containing at least 5 g/l to 55 g/l of carbohydrates and containing at least one amino-acid selected from the group consisting of glutamic acid, glutamine, arginine, tyrosine, threonine, aspartic acid, asparagine, proline, leucine and tryptophane, as well as any other amino-acids having a polysaccharide producing capacity at least equal under the same conditions and with the same total nitrogen content to 50% of that yielded by corn steep liquor, the source of nitrogen of said fermentation medium corresponding to a nitrogen value ranging from 0.1 g/l to 5 g/l; of cultivating said strain in said inoculated aqueous fermentation medium under aerobiosis and under stirred conditions with a pH value ranging from about 5.5 to 9 and at a temperature of 25° to 35° C; and of recovering said polysaccharide from the fermented aqueous medium.

9. A method according to claim 1, wherein said strain exhibits the following characteristics:

| | |
|---|---|
| Appearance on gelose | Round viscous yellow colonies |
| Gram | — |
| Gelatine | Slowly liquefied |
| Reduction of nitrates | — |
| Indole | — |
| Oxidase (Gordon and Mac Leod) | + |
| Citrate (Simmons) | + |
| Hugh Leifson | Oxidating |
| β-galactosidase | + |
| Urease | — |
| Tryptophane deseminase | — |
| Production of acetoin | + |
| Arginine dihydrolase | — |
| Lysine decarboxylase | — |
| Ornithine decarboxylase | — |
| Tolerance to sodium chloride | 1% to 2% |

10. A method according to claim 1, wherein the amino-acid which has been used to isolate said strain is contained in the fermentation medium in a proportion of at least 70%, expressed in terms of nitrogen, of the source of nitrogen of said fermentation medium.

11. A method according to claim 1, wherein the source of nitrogen of the fermentation medium consists of the mother liquor of crystallization of glutamic acid.

12. A method according to claim 1, wherein the source of nitrogen of the fermentation media consists of the by-products of agricultural and foodstuff origin the nitrogen content of which is mainly due to the amino-acids from said group.

13. A method according to claim 1 wherein the carbohydrates of said fermentation medium are selected from the group consisting of glucose, corn starch, starch hydrolysates, saccharose, levulose, fructose, maltose and sugar molasses.

14. A method according to claim 1, wherein the fermentation medium contains a source of magnesium in the form of soluble magnesium salts with a content of 0.0025 g/l to 1 g/l expressed in terms of magnesium.

15. A method according to claim 1, wherein the temperature used during the fermentation is at a value between 27° and 31°;0 C.

16. A method according to claim 1, wherein said pH value is between 6.5 and 8.

17. A method of isolating a novel strain of microorganism belonging to the Xanthomonas kind having an increased polysaccharide production output of at least 20 percent in terms of viscosity when compared to that achieved by *Xanthomonas campestris* NRRL-B-1459 when grown under the same conditions, consisting in effecting a selection of said strain from a swab taken from a sick plant through successive cultures in successive fractions of an isolating aqueous medium containing trace elements, a source of carbon, and a source of nitrogen with successive periods of incubation in each fraction of said medium, said source of nitrogen comprising a substantial amount of at least one amino-acid selected from the group consisting of glutamic acid, glutamine, arginine, tyrosine, threonine, aspartic acid, asparagine, proline, leucine and tryptophane.

18. A method of isolating a novel strain of microorganism belonging to the Xanthomonas type and filed with the American Type Culture Collection under Serial No. ATCC 31 176 on Oct. 14, 1975, consisting in effecting a selection of said strain from a swab taken from a sick plant through successive cultures in successive fractions of an isolating aqueous medium containing trace elements, a source of carbon, and a source of nitrogen, with successive periods of incubation in each fraction of said medium, said source of nitrogen comprising a substantial amount of at least one amino-acid selected from the group consisting of glutamic acid, glutamine, arginine, tyrosine, threonine, aspartic acid, asparagine, proline, leucine and tryptophane, said method comprising the steps of inoculating on said isolating medium yellow colonies of viscous appearance obtained through said cultures so as to dissociate various strains and then selecting said strain ATCC Serial No. 31 176 among the latter.

19. A method of producing a Xanthane type of polysaccharide comprising the steps of inoculating a strain of Xanthomonas in an aqueous fermentation medium, said strain being obtained from a sample taken from a sick plant by selection through successive cultures in an isolating aqueous medium containing trace elements, a source of carbon, and a source of nitrogen, said source of nitrogen comprising at least one amino-acid selected from a first group consisting of glutamic acid, glutamine, arginine, tyrosine, threonine, aspartic acid, asparagine, proline, leucine and tryptophane, said strain having an increased polysaccharide production output of at least 20 percent in terms of viscosity when compared to that achieved by *Xanthomonas campestris* NRRL-B-1459 grown under the same conditions in the presence of any one of the amino-acids of said first group but not growing in the presence of any one of the amino-acids selected from a second group consisting of glycocoll, lysine, cysteine, histidine, isoleucine and serine, when at least one amino-acid of said first group is absent, of cultivating said strain in said fermentation medium under aerobiosis and under stirred conditions with a pH value ranging from about 5.5 to 9 and at a temperature of 25° to 35° C, said fermentation medium containing sources of carbon and nitrogen comprising carbohydrates in an amount of 5 g/l to 55 g/l and 0.1 g/l to 5 g/l of total nitrogen, 70 to 100% of the total nitrogen of the fermentation medium being represented by the nitrogen from the amino-acids of said first group, and of then recovering said polysaccharide from the fermented aqueous medium.

20. A method of producing a Xanthane type of polysaccharide comprising the steps of inoculating a strain of Xanthomonas in an aqueous fermentation medium, said strain being obtained from a sample taken from a sick plant by selection through successive cultures in an isolating aqueous medium containing trace elements, a source of carbon, and a source of nitrogen, said source of nitrogen comprising at least one amino-acid selected from a first group consisting of glutamic acid, glutamine, arginine, tyrosine, threonine, aspartic acid, asparagine, proline, leucine and tryptophane, said strain having an increased polysaccharide production output of at least 20 percent in terms of viscosity when compared to that achieved by *Xanthomonas campestris* NRRL-B-1459 grown under the same conditions in the presence of any one of said first group but not growing in the presence of any one of the amino-acids selected from a second group consisting of glycocoll, lysine, cysteine, histidine, isoleucine and serine, when at least one amino-acid of said first group is absent, of cultivating said strain in said fermentation medium under aerobiosis and under stirred conditions with a pH value ranging from about 5.5 to 9 and at a temperature of 25° to 35° C, said fermentation medium containing sources of carbon and nitrogen comprising carbohydrates in an amount of 5 g/l to 55 g/l and 0.1 g/l to 5 g/l of total nitrogen, said fermentation medium containing at least one amino-acid selected from the first-named group and any other amino-acids giving a polysaccharide producing capacity at least equal to 50% of that yielded by corn steep liquor with said strain and in the same conditions of fermentation including the same total nitrogen content, and of then recovering said polysaccharide from the fermented aqueous medium.

* * * * *